(12) United States Patent
Motz et al.

(10) Patent No.: US 7,476,498 B2
(45) Date of Patent: Jan. 13, 2009

(54) PEPTIDES DERIVED FROM CAPSID ANTIGENS OF THE EPSTEIN-BARR VIRUS AND THE USE THEREOF

(75) Inventors: Manfred Motz, München (DE); Georg Bauer, Freiburg (DE); Erwin Soutschek, Berg (DE)

(73) Assignee: Mikrogen Molekularbiologische Entwickslung-GmbH, Neuried (DE)

( * ) Notice: Subject to any disclaimer, the term of this patent is extended or adjusted under 35 U.S.C. 154(b) by 322 days.

(21) Appl. No.: 11/192,070

(22) Filed: Jul. 29, 2005

(65) Prior Publication Data
US 2006/0057563 A1 Mar. 16, 2006

Related U.S. Application Data (63) Continuation of application No. PCT/EP2004/001127, filed on Feb. 6, 2004.

(30) Foreign Application Priority Data
Feb. 21, 2003 (DE) ................................ 103 07 517

(51) Int. Cl.
*C12Q 1/70* (2006.01)
(52) U.S. Cl. .......................................................... 435/5
(58) Field of Classification Search ........................ None
See application file for complete search history.

(56) References Cited

U.S. PATENT DOCUMENTS 5,424,398 A * 6/1995 Middeldorp et al. ........ 530/350

OTHER PUBLICATIONS

Hinderer et al (Journal of Clinical Microbiology 37:3239-3244, 1999).*
van Grunsven et al (Journal of Infectious Disease 170:13-19, 1994).*
Shedd et al ((Journal of Infectious Diseases 172:1367-1370, 1995).*
van Grunsven et al (Journal of Infectious Diseases 170:13-19, 1994).*
van Grunsven et al (Journal of Virology 67:3908-3916, 1993).*
English translation of International Preliminary Examination Report for PCT Appl. No. PCT/EP2004/001127 (Oct. 27, 2005).
Bauer, G. "Simplicity Through Complexity: Immunoblot With Recombinant Antigens as the New Gold Standard in Epstein-Barr Virus Serology," Clin. Lab. 2001;47:223-230.
Hinderer, W., et al., "Serodiagnosis of Epstein-Barr Virus Infection by Using Recombinant Viral Capsid Antigen Fragments and Autologous Gene Fusion," J. Clin. Microbiol. 1999;37(10):3239-3244.
Van Grusven, W.M.J., et al., "Localization and Diagnostic Application of Immunodominant Domains of the BFRF3-Encoded Epstein-Barr Virus Capsid Protein," J. Infec. Dis. 1994;170:13-19.
International Search Report for PCT Appl. No. PCT/EP2004/001127 (Jun. 14, 2004).

* cited by examiner

*Primary Examiner*—Mary E Mosher
(74) *Attorney, Agent, or Firm*—Shelly Guest Cermak; Cermak Kenealy & Vaidya LLP

(57) ABSTRACT

In the area of virus diagnosis, in particular Epstein-Barr virus (EBV) diagnosis, methods for the detection of EBV and agents suitable for this purpose are provided, including peptides which are derived from p18-VCA and permit discrimination between acute and past EBV infection.

2 Claims, 7 Drawing Sheets

A: Past EBV infections

Reaktionskontrolle = Reaction control          Cut-off-Kontrolle = Cut-off control
Trennlinie = Separation line                   IgG-Konjugatkontrolle = IgG conjugate control

B: Recent EBV infections

Reaktionskontrolle = Reaction control          Cut-off-Kontrolle = Cut-off control
Trennlinie = Separation line                   IgG-konjugatkontrolle = IgG conjugate control Fig. 4: Mikrogen/Viramed strip comparison

FRISCHE INFEKTIONEN = RECENT INFECTIONS

B

ABGELAUFENE INFEKTIONEN = PAST INFECTIONS

Note: Intermediate stages in the Mikrogen test arose from the measurement with the aid of the Appollo blot processor. The OD determined in the scan was correlated with the semiquantitative ++ evaluation by means of a calibration curve.

```
  1 MARRLPKPTL QGRLEADFPD SPLLPKFQEL NQNNLPNDVF REAQRSYLVF LTSQFCYEEY
 61 VQRTFGVPRR QRAIDKRQRA SVAGAGAHAH LGGSSATPVQ QAQAAASAGT GALASSAPST
121 AVAQSATPSV SSSISSLRAA TSGATAAASA AAAVDTGSGG GGQPHDTAPR GARKKQ
```

PEPTIDES DERIVED FROM CAPSID ANTIGENS OF THE EPSTEIN-BARR VIRUS AND THE USE THEREOF

This application is a continuation under 35 U.S.C. §120 of PCT/EP04/01127, filed Feb. 6, 2004.

BACKGROUND OF THE INVENTION

1 Field of the Invention

The present invention relates to the area of viral diagnosis, in particular Epstein-Barr virus (EBV) diagnosis. Improved methods for the detection of EBV infections and agents suitable for this purpose are provided.

2 Brief Description of the Related Art

The Epstein-Barr virus is a human herpes virus which is considered to be the trigger of infectious mononucleosis. Infection with EBV often takes place subclinically, occasionally with mild symptoms. In immunosuppressed persons, however, an EBV infection can lead to severe malignant manifestations.

Importance of Epstein-Barr Virus (EBV) Diagnosis

EBV diagnosis is of considerable differential diagnostic importance since the symptoms of acute EBV infection may overlap with many clinical pictures which are caused by other pathogens or have other causes. Thus, an acute EBV infection may be confused with a primary HIV infection, rubella virus infection, cytomegalovirus infection, infection by classical hepatitis viruses, toxoplasmosis, leptospirosis, infection by various neurotropic pathogens and with leukaemia or a lymphoma. Unambiguous EBV serology therefore constitutes a major obligation to the patient.

Problems of EBV Serology

Classical EBV serology is based on the detection of the IgG and IgM antibody response to viral capsid antigens (VCA) and to EBV-specific nuclear antigens (EBNA), in particular EBNA-1.

The classification of various EBV antigen classes is based on the biological cycle of virus multiplication with proteins required early (EA) and late (VCA) and antigens for maintaining the latency (EBNA). These antigen classes were detectable and distinguishable in the first serological test systems (immunofluorescence with EBV-infected cells). All further subsequent developments of serological test systems retained this scheme and thus permit the distinction of antibody specificities with respect to EBNA, VCA and EA.

The VCA and EBNA markers were first defined in the immunofluorescence technique. In more recent tests, the purified components p18 and p23 of the VCA complex, which are generally prepared by a recombinant method and p72, which corresponds to EBNA-1, are used. The EBNA-1 antigen is formed at a late stage after an initial infection with the establishment of cells with latent infection and is one of the factors responsible for maintaining this status. This means that anti-EBNA-1 is formed only after the elapse of up to six months following initial infection. At the same time, however, it also means that, when this marker is present, diagnosis can safely exclude a recent infection, and thus an important marker for assignment of the time of infection is available.

EBV serology has a high degree of variability, frequently leading to ambiguous or false results if only the classical markers VCA-IgG, VCA-IgM and anti-EBNA-1 are determined. Thus, for example, not all acute EBV infections have a detectable VCA-IgM response, so that in this case test strategies which are based only on the determination of VCA-IgG and VCA-IgM lead to a false conclusion. On the other hand, a VCA-IgM response can in rare cases also persist for months and thus simulate a recent infection.

Positive anti-EBNA-1 is evidence of an elapsed EBV infection and, in combination with positive VCA-IgG, is the only unambiguous serological constellation. Negative anti-EBNA-1 (with simultaneously positive VCA-IgG) either may indicate an acute EBV infection or may be caused by secondary anti-EBNA-1 loss in the case of immunosuppression In addition, about 5% of those infected never develop detectable anti-EBNA-1 and thus simulate the serological situation of an acute EBV infection for their whole life.

Thus, an acute EBV infection is safely ruled out by simultaneous positive VCA-IgG and anti-EBNA-1. However, positive VCA-IgG with negative anti-EBNA-1 represents an ambiguous constellation which occurs in three situations:
1) in case of recent EBV infection;
2) in case of elapsed infection and anti-EBNA-1 loss through suppression of the cellular immune system;
3) in case of elapsed infection and simultaneous lack of anti-EBNA-1 formation (in about 5% of the healthy population).

Cases 2) and 3) are, for example, to be found more frequently than true recent EBV infection among patients examined in major hospitals.

This key problem of EBV serology could be reliably solved to date only by complicated, additional tests or by repetitions over a period of time in association with clinical data.

The lack of anti-EBNA-1 is therefore generally used as an indicator of a fresh infection. As mentioned above, this can lead to drastic misinterpretations in the case of EBV-infected persons who remain anti-EBNA-1-negative or, because of suppression of the cellular immune system, lose the relevant antibodies. The current methods used in routine diagnosis and employing anti-EBNA-1 do not safely permit the diagnosis of a fresh EBV infection.

The differentiation of primary anti-EBNA-1 negativity in acute EBV infection on the one hand and anti-EBNA-1 loss and lack of anti-EBNA-1 formation on the other hand is therefore the major problem of EBV serology. This particular problem is not taken into account in most published evaluations of serological tests. It must be assumed that up to 20 percent of the examinations for EBV infection are ambiguous and lead to incorrect findings. These are of major importance particularly in oncology, transplantation medicine and care during pregnancy.

SUMMARY OF THE INVENTION

It is an aspect of the present invention is to provide agents for the detection of an EBV infection which permit a safe differentiation between acute infection and past infection.

BRIEF DESCRIPTION OF THE DRAWINGS

The figure schematically shows, in the upper half, a conventional immune blot for determining antibodies against EBV and, in the lower half, a test according to the invention which additionally comprises p18 antigens shortened at the N-terminus (indicated on the strip as "p18". The markers p23 (VCA), p54 (early antigen) and p138 (early antigen) are seropositivity markers which cannot differentiate between fresh infections and past infections. The antibody response to these markers is variable so that different patterns of the immune response may be detectable. Positivity of the antibody response to at least one of these markers permits the diagnosis "EBV-infected", without further differentiation between "recent infection" and "past infection". A positive IgG response to p72 (=EBNA-1) permits the reliable diagnosis "past infection". In the conventional test, the classical past EBV infection (A1) is correctly recognized on the basis of the positive p72-IgG whereas a past EBV infection without p72-IgG formation (A2) or a past EBV infection with subsequent secondary p72-IgG loss (A3) cannot be differentiated from a true recent EBV infection (B) with as yet no p72-IgG response. The cases A2 and A3 are as a rule therefore incorrectly diagnosed in the conventional test. In daily practice, these cases are, however, more frequent than the true recent EBV infections.

With the use of the modified test (lower half) which comprises, for example, p18 shortened at the N-terminus (indicated as "p18" in FIG. 1), the recent EBV infection with lack of p18-IgG (B) is clearly differentiated from the past EBV infections (A1-A3), even when p72-IgG is absent.

FIG. 2 shows the expression of various peptides. A Coomassie blue-stained SDS polyacrylamide gel of lysates of the expressing *E. coli* clones after induction is shown (cf. Example 1). The lanes correspond to the following batches:
Lane 1: Expression of p18 shortened at the N-terminus (p18-30)
Lane 2: Expression of total p18 in pDS vector
Lane 3: Expression of total p18 in pQE vector
Lane 4: Molecular weight marker The differences in magnitude of the total p18 antigen are based on different N-terminal amino acids; the pQE vector has an additional histidine tag. The p18 shortened at the N-terminus has, as expected, a molecular weight which is about 4 kDa lower.

FIG. 3 shows the reactivity of the peptides in the immune blot. Lysates of induced *E. coli* clones with the two p18 variants were separated by gel electrophoresis and then transferred to nitrocellulose membranes (Western Blot).
Lane 1: Total p18 without His tag
Lane 2: p18-30 (shortened p18 version)

The nitrocellulose membranes were incubated with sera from EBV-positive persons; specifically bound antibodies were then visualized with a peroxidase-conjugated second anti-IgG antibody and TMB staining.
A; serum of a patient with recent EBV infection
B; serum with former EBV infection

In each case 10 sera of persons with former EBV infection but problematic serology (weak antibody titre, lack of anti-EBNA-1; A) and 10 samples from patients with a recent EBV infection (B) were tested using two versions of EBV antigen strips:

"Mikrogen" strips comprise the additional EBV antigens EBNA-1, p23 (VCA) and p54 and p138 (EAs) apart from p18 shortened at the N-terminus.

Viramed strips also comprise EBV proteins EBNA- 1, EA-p54 and gp125 (VCA) apart from a complete p18 antigen.

In the left half (Mikrogen test), "p18" denotes p18 shortened at the N-terminus. In the right half (Viramed test), "p18" denotes the viral full-length p18.

In the case of the former infections (A), a more or less pronounced anti-p18 reaction is to be found in both tests.

Sera of patients after recent infection (B), however, do not show a reaction in any case in the test with p18 shortened at the N-terminus, but in all samples with the ViraStripe (total p18).

32 samples of patients with recent EBV infection ("acute") and 25 serum samples of persons with past (old) EBV infection were each tested with p18 shortened at the N-terminus (sprayed on nitrocellulose strips, Mikrogen (cf. antigen strips from FIG. 4)) and a commercial ELISA (from Sorin) with conventional p18-VCA antigen.

In the two diagrams, in each case the ODs of the two tests are plotted against one another; x axis—intensity of the band with p18 shortened at the N-terminus; y axis—ELISA values with total p18. The OD values of the ELISA were determined by means of a customary ELISA reader and are between 0 and 3.0; the nitrocellulose strips with the p18 shortened at the N-terminus were scanned in and the intensity of the band was determined by means of a software program; here, the scale comprises values from 0 to 200. The two additional lines represent the respective cut-offs.

FIG. 6 shows the correlation of the p18 reactivity in various test formats. The results of the testing of sera with recent and past infections from Example 4 (FIG. 5) were additionally investigated in strip tests with conventional VCA-p18 (from Viramed) and the results were correlated with the VCA-ELISA values and the reactivity with the p18 shortened at the N-terminus.

The graphic evaluation was effected in a manner similar to that described in the preceding example: x axis with the ELISA OD values (from 0 to 2.0); y axis with p18 reactivities of the two strip tests (circles—Viramed with total p18; dots—p18 antigen shortened at the N-terminus).

DESCRIPTION OF THE PREFERRED EMBODIMENTS

Surprisingly, it was found that, by modifying the viral EBV capsid antigen p18, it was possible to obtain a peptide which reacts with antibodies which are formed with a similar certainty to anti-EBNA-1 only at a late stage after infection and do not exhibit the problem of nonformation or loss in immunosuppressed persons to the same extent.

These are peptides which are derived from the EBV-p18 antigen which is coded by the reading frame BFRF3. This antigen was described as a VCA marker as long ago as 1988 (Middeldorp and Herbrink, J. Virol. Meth., 21 (1988) 133-146).

The molecular assignment of p18 and the preparation of the protein by means of genetic engineering methods and the use of certain immunologically active fragments thereof are described in EP 574 075 A2. However, the description of the properties of the recombinant antigens or of the chemically synthesized fragments was always based on optimum reactivity.

IgG antibodies against a purified complete p18 antigen prepared by a recombinant method are detectable even in the case of a recent EBV infection and are therefore not suitable for discriminating between acute infections and past infections.

Surprisingly, it has been found in the course of investigations that a discrimination of antibody responses as a function of time is achieved, for example, by omitting the N-terminal region of the p18 antigen: N-terminally deleted p18 recognizes antibodies which are formed only weeks after infection.

The present invention therefore relates to a peptide which is derived from the viral p18 antigen of the Epstein-Barr virus and wherein said peptide reacts with antibodies from individuals having an Epstein-Barr virus infection dating back to the relatively distant past, but not or weakly with antibodies from individuals having an acute Epstein-Barr virus infection or an Epstein-Barr virus infection which dates back to the recent past.

The expression "peptide" includes oligopeptides and polypeptides. The length of the peptides is not limited, unless it is stated.

The peptide according to the invention is a modified p18 antigen, i.e. it is not identical to the viral p18, the "wild type protein". The modifications relative to the viral p18 are not particularly restricted, provided that the modified peptide reacts with antibodies from individuals having an EBV infection dating back to the relatively distant past, but not or weakly with antibodies from individuals having an acute EBV infection or EBV infection dating back to the recent past.

The fact that the peptide according to the invention is derived from p18 means that it comprises at least one fragment having at least one epitope of the complete viral p18 antigen. Such an epitope is present if a positive reaction is obtained in a line assay (cf. Example 3) on incubation with sera from individuals having an EBV infection dating back to the relatively distant past.

Figure 7:
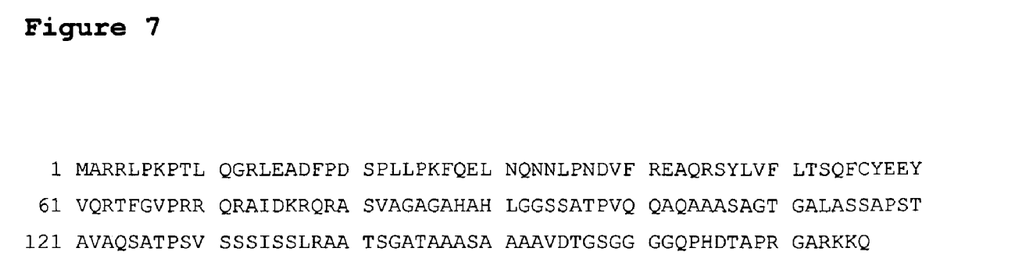
FIG. 7 shows the amino acid sequence of the viral p18 (SEQ ID NO:1

The amino acid sequence of the viral p18 is shown in FIG. 7 (SEQ ID NO:1). As a rule, the peptide according to the invention has an amino acid sequence differing from SEQ ID NO:1. It preferably comprises one or more deletions and/or substitutions. Most preferably, the peptide according to the invention has one or more deletions compared with the amino acid sequence represented in SEQ ID NO:1. Amino acids may be deleted at the N-terminus of p18, but also at the C-terminus and/or at internal positions of the p18 sequence. Preferably, one or more amino acids of the N-terminus of the p18 sequence are deleted.

The peptide according to the invention comprises or consists of at least 10 successive amino acids of the amino acid sequence SEQ ID NO:1, preferably at least 25, more preferably at least 50, even more preferably at least 75, even more preferably at least 100, most preferably at least 125, successive amino acids of the amino acid sequence SEQ ID NO:1.

It is preferable if at least one epitope of the complete p18-VCA, against which antibodies are formed after infection, is not present in the peptide according to the invention.

As a rule, the peptide according to the invention is 1 to 100 amino acids, preferably 5 to 90 amino acids, more preferably 10 to 70 amino acids, even more preferably 15 to 50 amino acids, even more preferably 20 to 40 amino acids, most preferably about 30 amino acids, shorter at the N-terminus than the viral p18 antigen. In a preferred embodiment, the peptide according to the invention consists of the amino acid sequence SEQ ID NO:2. This amino acid sequence corresponds to the amino acids 31 to 176 of SEQ ID NO:1. In further preferred embodiments, the peptide according to the invention has substantially an amino acid sequence which is selected from the group consisting of
amino acids 21 to 176 of SEQ ID NO:1,
amino acids 22 to 176 of SEQ ID NO:1,
amino acids 23 to 176 of SEQ ID NO:1,
amino acids 24 to 176 of SEQ ID NO:1,
amino acids 25 to 176 of SEQ ID NO:1,
amino acids 26 to 176 of SEQ ID NO:1,
amino acids 27 to 176 of SEQ ID NO:1,
amino acids 28 to 176 of SEQ ID NO:1,
amino acids 29 to 176 of SEQ ID NO:1,
amino acids 30 to 176 of SEQ ID NO:1,
amino acids 31 to 176 of SEQ ID NO:1,
amino acids 32 to 176 of SEQ ID NO:1,
amino acids 33 to 176 of SEQ ID NO:1,
amino acids 34 to 176 of SEQ ID NO:1,
amino acids 35 to 176 of SEQ ID NO:1,
amino acids 36 to 176 of SEQ ID NO:1,
amino acids 37 to 176 of SEQ ID NO:1,
amino acids 38 to 176 of SEQ ID NO:1,
amino acids 39 to 176 of SEQ ID NO:1,
amino acids 40 to 176 of SEQ ID NO:1 and
amino acids 41 to 176 of SEQ ID NO:1.

The person skilled in the art is also aware that the immunological properties of said sequences are often changed only insignificantly if amino acids are inserted, substituted or deleted. Substitutions which are often regarded as being conservative are those in which the chemical nature of the substituting amino acid is similar to that of the substituted amino acid. Amino acid combinations which may be regarded as being conservative are, for example, Gly/Ala, Asp/Glu, Asn/Gln, Val/Ile/Leu, Ser/Thr, Lys/Arg and Phe/Tyr.

The peptide according to the invention may also be one or more C-terminal amino acids shorter than the viral p18 without losing its functionality. Usually, not more than 10 amino acids, more preferably not more than 5, most preferably not more than 2, amino acids are absent at the C-terminus compared with p18. In particular developments, the peptide substantially comprises an amino acid sequence which is selected from the group consisting of the sequences
amino acids 31 to 166 of SEQ ID NO:1,
amino acids 31 to 167 of SEQ ID NO:1,
amino acids 31 to 168 of SEQ ID NO:1,
amino acids 31 to 169 of SEQ ID NO:1,
amino acids 31 to 170 of SEQ ID NO:1,
amino acids 31 to 171 of SEQ ID NO:1,
amino acids 31 to 172 of SEQ ID NO:1,
amino acids 31 to 173 of SEQ ID NO:1,
amino acids 31 to 174 of SEQ ID NO:1 and
amino acids 31 to 175 of SEQ ID NO:1.

However, it is preferable if the peptide according to the invention is not shortened at the C-terminus compared with the viral p18.

It is possible to add additional amino acids or chemical groups at the N- or C-terminus in order to create a sort of "linker" by means of which the peptide can advantageously be coupled to a carrier. Such a "linker" has, as a rule, 1 to 60 amino acids, but in general 1 to 10 amino acids. The binding of the peptide to a carrier or a solid phase need not however be covalent. It is also possible to add cysteine residues in order to achieve coupling to other peptides.

The peptides according to the invention can be further modified, for example by glycosylation, amidation, carboxylation or phosphorylation. The invention also relates to functional derivatives, such as, for example, salts, amides, esters, C-amidated or N-acylated derivatives.

On the basis of the information in this Application, the person skilled in the art can easily determine whether a certain p18 derivative is suitable for differentiating between acute infection and past infection. For this purpose, for example, a given p18 derivative need only be tested in a line assay as described in Example 3.

The peptides according to the invention can be prepared by various methods known to the person skilled in the art. As a rule, they are prepared either by chemical synthesis or by expression of recombinant DNA in suitable host cells.

Solid-phase synthesis or liquid-phase synthesis can be used as methods for the chemical synthesis of peptides. Solid-phase synthesis is preferred. Methods for the chemical synthesis of peptides are described in Bodanszky and Ondetti: Peptide Synthesis, Interscience Publishers, New York (1966); The Peptides, Analysis, Synthesis, Biology, Volume 1-3 (Ed. Gross and Maienhofer) 1979, 1980, 1981 (Academic Press, Inc.).

For the recombinant preparation of the peptide according to the invention, a nucleic acid which codes for the amino acid sequence of the peptide is first provided. The nucleic acid may be DNA or RNA, DNA being preferred. The coding nucleic acid is usually introduced into a vector or a plasmid which contains suitable sequences which permit the expression of the coded peptide. Suitable sequences of this type are, for example, a promoter, a terminator sequence and sequences which permit replication of the plasmid. They may be expression plasmids for expression in prokaryotes or in eukaryotes. The person skilled in the art is aware that different promoter sequences are used. Prokaryotic expression plasmids are preferred.

The invention also relates to a vector or a plasmid which contains a nucleic acid which codes for a peptide according to the invention. Customary methods for the preparation of vectors and plasmids are described in Sambrook et al., Molecular Cloning: A Laboratory Manual, 2001, Cold Spring Harbour Laboratory Press. Furthermore, the vector or the plasmid is introduced into a suitable host organism, for example mammalian cells or preferably bacteria, which is then cultivated under suitable conditions so that expression of the desired peptide takes place. The invention also relates to a cell comprising a vector according to the invention or a plasmid according to the invention. A further aspect of the invention is a method for the preparation of a peptide according to the invention, which comprises cultivating cells according to the invention under suitable conditions so that the desired peptide is expressed, and optionally recovering the peptide. After expression is complete, the peptide can be recovered by methods known per se to the person skilled in the art. Suitable methods for the recombinant expression of peptides are described in Molecular Cloning: A Laboratory Manual by Sambrook et al. (see above).

The peptide is preferably present in isolated form, i.e. it is substantially free of other peptides. The purity of the peptide according to the invention is preferably greater than 90%, more preferably greater than 95%, most preferably greater than 99%, determined by SDS-PAGE with subsequent Coomassie staining.

After expression is complete, the peptide is as a rule therefore purified. A very wide range of purification methods known to the person skilled in the art may be used. Methods for the purification of proteins and peptides are described in Methods in Enzymology, Vol. 182, Guide to Protein Purification, Academic Press, New York 1990 or Scopes R. K., Protein Purification, Springer-Verlag, Heidelberg 1994.

The peptide according to the invention is distinguished by the fact that it reacts with antibodies from individuals having an Epstein-Barr virus infection dating back to the relatively distant past, but not or weakly with antibodies from individuals having an acute Epstein-Barr virus infection or an Epstein-Barr virus infection dating back to the recent past. Preferably, the peptide does not react with antibodies from individuals having an EBV infection dating back to the recent past. The data preferably relate to IgG antibodies.

Sera from individuals having an infection dating back to the relatively distant past may have the following serological properties:
anti-EBNA-1-IgG: positive;
anti-p23-IgG: positive;
anti-p54-IgG: negative;
anti-p138-IgG: negative; and
anti-p23-IgM: negative.

The peptide according to the invention reacts with antibodies from sera which have these serological properties.

As a rule, an infection dating back about 1.5 years may be defined as an "infection dating back to the relatively distant past".

The infection of an individual with EBV is considered to be "acute" if the clinical picture of infectious mononucleosis is present. Sera from an individual having an EBV infection dating back to the recent past may have the following serological properties:
anti-EBNA-1-IgG: negative;
anti-p54-IgG and/or anti-p138-IgG (EA): positive;
anti-p23-IgG (VCA): positive; and
anti-p54-IgM and/or anti-p138-IgM and/or anti-p54-IgM: positive.

The peptide according to the invention does not react or reacts weakly with antibodies from sera which have these serological properties.

As a rule, an infection dating back about 4 weeks may be defined as an "infection dating back to the recent past"

In the context of the present Application, the expression that a peptide "reacts" with antibodies means that the peptide forms antigen-antibody immune complexes with one or more antibodies after the peptide and antibody have been brought into contact with one another. No reaction or a weak reaction with the peptide with antibodies is present if no antigen-antibody complexes or only weak antigen-antibody complexes are formed after peptide and antibody have been brought into contact with one another. Whether a peptide reacts with antibodies can be determined by a "line assay", as described in Example 3.

The invention furthermore relates to a fusion peptide, which comprises an above-described peptide according to the invention, and one or more further amino acids which do not correspond to the amino acid sequence of the viral p18 antigen. A very wide range of foreign sequences may be involved. However, it is preferable if only a few foreign amino acids are contained in the fusion peptide, in order to avoid a cross reaction of the foreign amino acids with antibodies. Examples of foreign sequences are amino acid sequences which facilitate the affinity purification of the expressed peptide, for example an oligohistidine stretch (6 to 8 successive histidine residues) at the N- or C-terminus.

A further aspect of the invention is a diagnostic reagent for the detection of antibodies against Epstein-Barr virus, comprising a peptide according to the invention and/or a fusion peptide according to the invention. A "diagnostic reagent" in the context of the present invention comprises a solid phase or a tracer. Solid phases may be, for example, micro test plates, cells, vessels, membranes, filters, test strips or particles, such as beads. Methods for binding peptides to solid surfaces or solid phases are known per se to the person skilled in the art.

Tracers may be, for example, radioactive isotopes, fluorescent compounds, enzymes, stains, etc. The peptides or fusion peptides according to the invention may be marked or unmarked, depending on the intended use. The marking may be of any kind, for example enzymatic, chemical, fluorescent, luminescent or radioactive.

Antibodies against Epstein-Barr virus can be detected, for example, by bringing a diagnostic reagent according to the present invention into contact with serum which originates from an individual and then detecting the antigen-antibody complexes formed. The invention therefore also relates to a method for the detection of antibodies against Epstein-Barr virus in a sample, which comprises bringing a peptide or fusion peptide according to the invention or diagnostic reagent according to the invention into contact with the sample and then detecting the antigen-antibody complexes formed.

The sample is as a rule body fluid which originates from an individual. Preferably, the sample is serum which originates from an individual. The serum may be diluted with a suitable liquid.

In the method according to the invention, a diagnostic reagent described above is usually used. Depending on the nature and further features of the diagnostic reagent, the immunochemical reaction is a so-called sandwich reaction, an agglutination reaction, a competition or an inhibition.

In a preferred format of the method, the peptide or fusion peptide according to the invention is immobilized on a solid phase. The solid phase is then brought into contact with the sample to be investigated, for example serum, with the result that antigen-antibody complexes can form. The solid phase is then washed once or several times in order to remove bound antibodies. Immobilized antigen-antibody complexes are then identified. This can be effected, for example, by so-called anti-antibodies which are coupled to a marker. Thus, after washing, the solid phase can be brought into contact with an anti-IgG antibody which is coupled to horseradish peroxidase. This anti-antibody binds to the immobilized immune complex. The bound secondary antibody can be visualized in a known manner by the enzyme reaction of the horseradish peroxidase. The secondary antibody preferably specifically recognizes human IgG.

Membranes or test strips on which one or more antigens are immobilized are preferably used in the method. In another embodiment of the method, an ELISA test is carried out. The procedure for such methods is known per se to the person skilled in the art. An overview of suitable detection methods is to be found in "Labor und Diagnose" [Laboratory and Diagnosis], L. Thomas; Die medizinische Verlagsgesellschaft, Marburg; ISBN 3-921320-21-6.

For carrying out an ELISA, a peptide or a mixture of a plurality of peptides is usually bound to a solid phase, for example to a microtitre plate. A suitable dilution of the body fluid (serum) to be tested is brought into contact with the solid phase with which the peptide or peptides is or are bound. The subsequent incubation is carried out for a period which is sufficient for the formation of antigen-antibody complexes. Unbound components are then washed off. The detection of the immune complexes is effected as a rule by means of antibodies which bind specifically to human immunoglobulins and which are labelled (for suitable markers, see above). After addition of a substrate, a product which can easily be detected visually, photometrically, spectrometrically, luminometrically or electrochemically is then often formed.

Another variant is the competition assay, which is also known to the person skilled in the art.

In a particular embodiment of the method, a further antigen of the Epstein-Bar virus is brought into contact with the sample, and the antigen-antibody complexes formed are then detected. A further antigen of the EBV is preferably an antigen which is characteristic of a recent infection. The further antigen is preferably selected from the group consisting of p18, p23, p138 and p54. In a further embodiment of the method, the late nuclear antigen EBNA-1 (p72) is used in addition to the peptide or fusion peptide according to the invention. In a further embodiment, the antigens p72, p18, p23, p138 and/or p54 are used in addition to the peptide or fusion peptide according to the invention.

A further aspect of the invention is a test kit for the detection of antibodies against the Epstein-Barr virus, which comprises a peptide or fusion peptide according to the invention and/or a diagnostic reagent as described above. The test kit may comprise further agents suitable for carrying out the method according to the invention, for example a composition which comprises a secondary antibody. The test kit preferably comprises a solid phase. Western Blot test strips on which at least one peptide or fusion peptide according to the invention is immobilized are particularly preferred. Further EBV antigens can be mobilized, e.g. p18, p23, p72, p54 and/or p138. The strips may be nitrocellulose strips. The test kit may furthermore comprise wash solutions, optionally in concentrated form.

A further aspect of the invention is the use of a modified virus capsid antigen of the Epstein-Barr virus for determining whether an acute EBV infection/EBV infection dating back to the recent past or dating back to the relatively distant past/a past EBV infection is present. The preferred embodiments of the use according to the invention correspond to the above-described preferred embodiments of the peptide, of the fusion peptide, of the diagnostic reagent, of the test kit and/or of the method. The invention furthermore relates to the use of a modified virus capsid antigen of the Epstein-Barr virus for the serological discrimination of recent infections/infections dating back to the recent past and past infections. The invention furthermore relates to the use of a modified virus capsid antigen of the Epstein-Barr virus for the detection of antibodies against EBV. It is preferably possible to distinguish between recent infection and a past infection. The invention furthermore relates to the use of a modified virus capsid antigen of the Epstein-Barr virus for the detection of a past EBV infection. Finally, the invention relates to the use of a modified virus capsid antigen of the Epstein-Barr virus for differentiating between a past EBV infection and a recent EBV infection. The modified virus capsid antigen according to the uses of the invention preferably corresponds to the peptide or fusion peptide according to the invention. All further preferred variants of the invention which are described above apply in context to the uses of the invention.

All aspects and preferred embodiments of the invention which are described in the present Application can be combined with one another in a very wide variety of ways. The invention likewise relates to such combinations.

In addition to EBNA-1, the present invention provides a second late marker which additionally does not have the problem of a nonformation of antibodies. In contrast to EBNA-1, antibodies against p18 are not lost after cellular immunosuppression. The identification of IgG against a p18 modified according to the invention accordingly reliably excludes an acute EBV infection.

By using modified p18 in suitable measuring systems, such as, for example, the immune blot, it is therefore possible to detect recent EBV infections and past EBV infections even when the anti-EBNA response is atypical.

The following examples explain the invention in more detail.

EXAMPLE 1

Recombinant Preparation of Total p18 and p18 Antigen Shortened at the N-Terminus The expression cloning of an antigen which compared with a viral total p18 lacks 30 amino acids at the N-terminus is described as an example of a p18 shortened at the N-terminus.

The region coding for the amino acids 31-176 of the p18 antigen was amplified by means of PCR and corresponding oligonucleotide primers from isolated EBV-DNA (B95-8 strain).

(Reading frame BFRF3; sequence data according to genetic sequence database entry)

```
Primer for total p18:
5'-primer:
GAG GGA TCC ATC ATG AAA CGC GGG CTG    (SEQ ID NO:3)
CCC AAG CCC ACC 3'-primer:
CGC CTG CAG TTA CTG TTT CTT ACG TGC    (SEQ ID NO:4)
CCC GCG Primer for shortened p18:
5'-primer:
GAG GGA TCC CTG AAC CAG AAT AAT CTC    (SEQ ID NO:5)
CCC 3'-primer
CGC CTG CAG TTA CTG TTT CTT ACG TGC    (SEQ ID NO:6)
CCC GCG
```

Nucleotides in bold correspond to p18-coding sequences; nucleotides in italics represent restriction enzyme interfaces which were used for further cloning steps (GGATCC-BamH1; CTGCAG-Pst1).

The PCR was carried out in 100 µl batches with standard methods and using standard buffers (denaturing at 94° C. for 1 min; primer binding at 55° C. for 1 min; synthesis at 72° C. for 1 min; 40 cycles altogether).

After checking of the PCR products for correct size in the gel electrophoresis (about 530 nt for total p18 and about 440 nt for shortened p18), both were purified and desalinated by means of conventional methods, then cut with BamH1 and Pst1 and finally inserted into the corresponding positions of the expression vector pDS1. pDS1 is a vector with ampicillin resistance and an optimized lac promoter and subsequent translation start with the BamH1 and Pst 1 position which impart correct translation of the PCR products in the right reading frame.

Other expression systems are also suitable.

For comparison purposes, the total p18-coding fragment is also finally inserted into the commercial vector pQE30 (QIAGEN).

After transformation, E. coli clones with expression plasmid and correct inserts were induced by standard methods, and the lysates were analyzed by SDS gel electrophoresis and subsequent Coomassie staining.

Both batches show clear expression of recombinant p18 or p18 derivative. The total p18 has a molecular weight of about 22 kDa, and the protein shortened at the N-terminus by 30 amino acids has a size of about 18 kDa with a somewhat lower expression yield.

Figure 1:
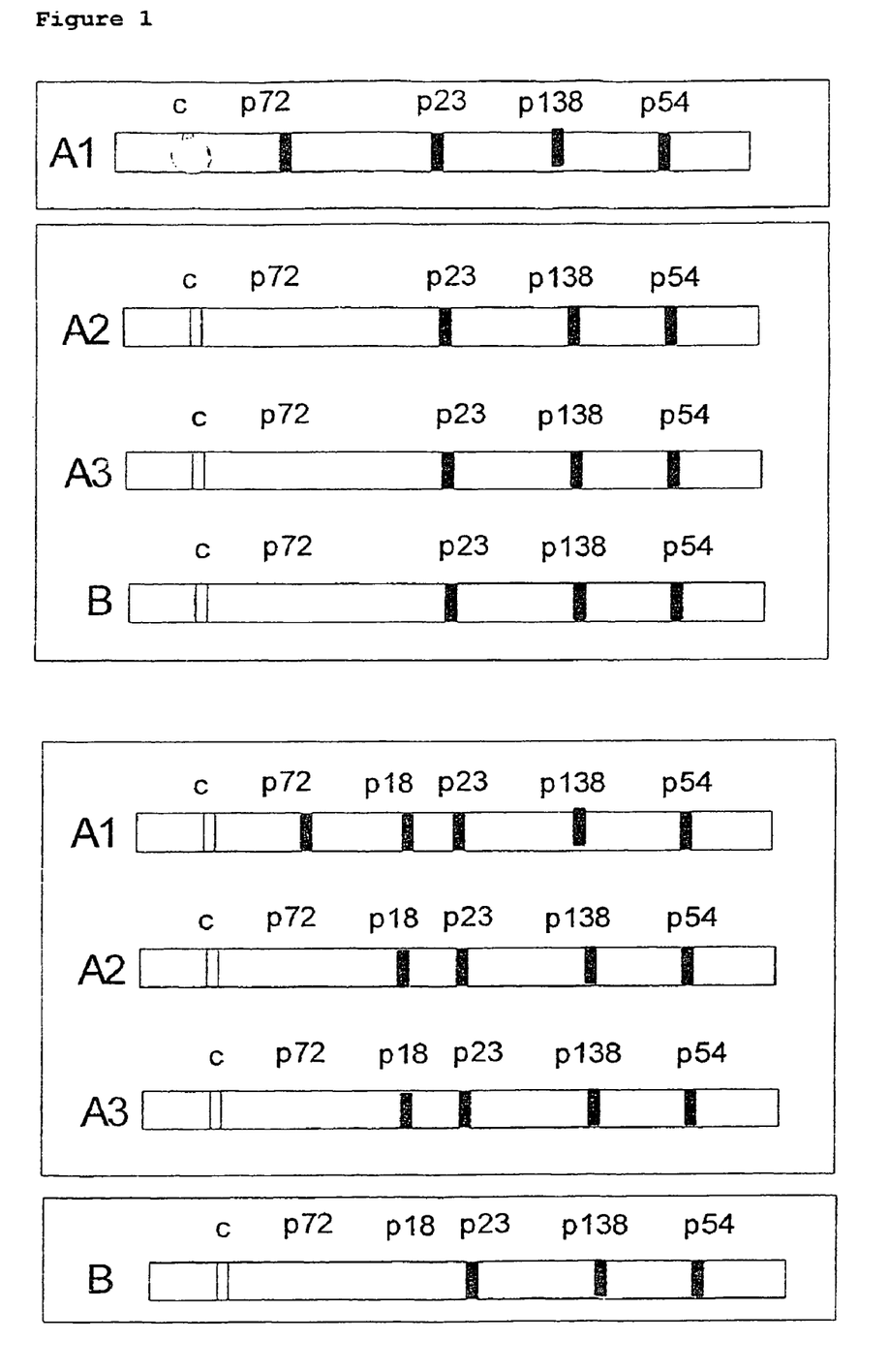
FIG. 1 shows the improvement in the informative power of the EBV diagnosis through the use of a modified p 18 antigen.
Figure 2:
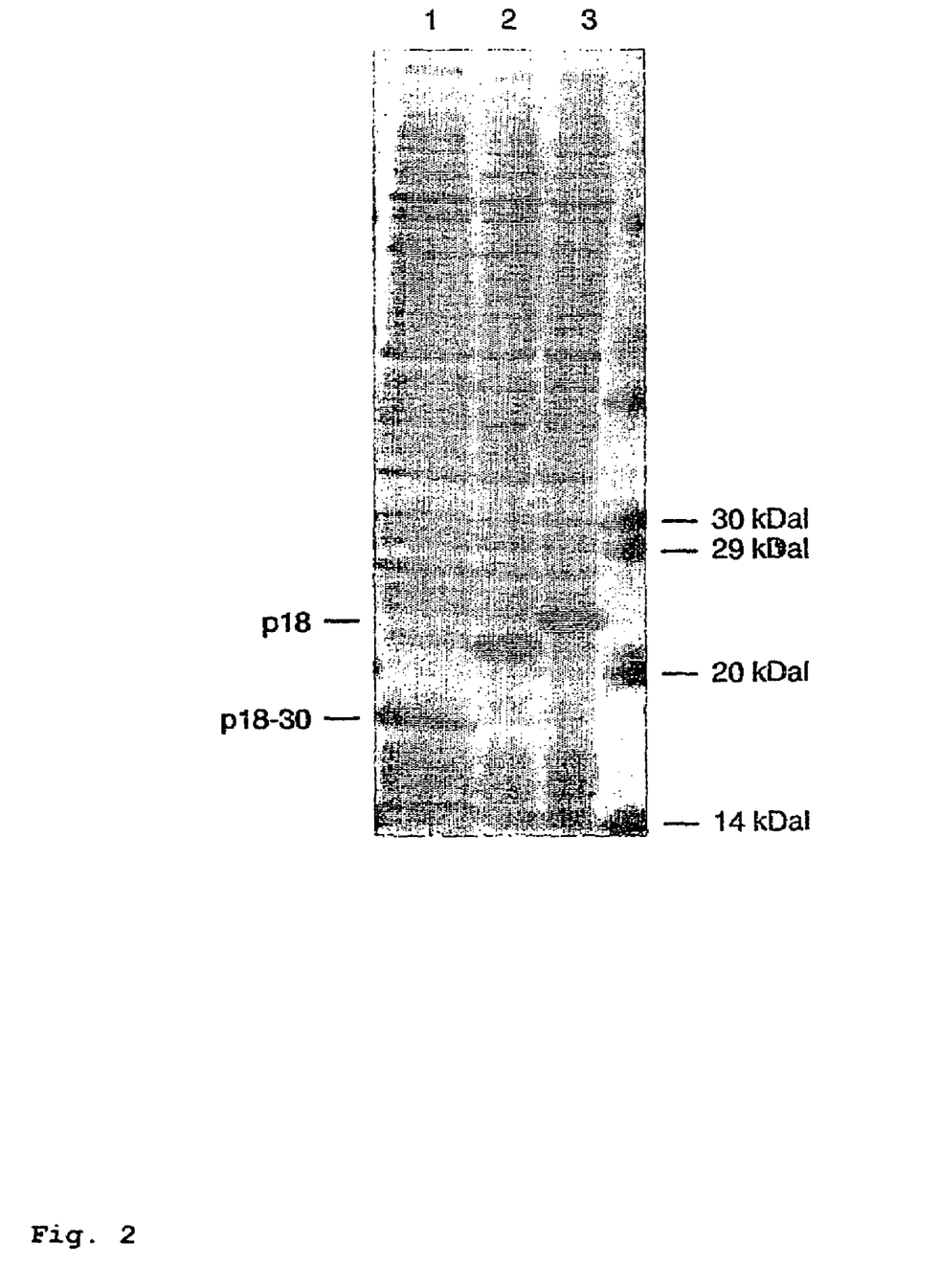

The pQE30 expression of the total p18 has a yield in a similar range, and the product is somewhat larger owing to the additionally present histidine residues (FIG. 2).

EXAMPLE 2

Comparison of the Reactivity of Total p18 with Antigen Shortened at the N-Terminus The lysates of the clones with total and shortened p18 were once again separated by gel electrophoresis, transferred to nitrocellulose and then investigated with regard to their reactivity with various EBV-positive sera.

For this purpose, the nitrocellulose membranes were incubated with sera diluted 1:100 and specific antibodies were visualized with a second peroxidase-conjugated antibody and subsequent staining reaction.

Buffers, dilutions and incubation times were carried out analogously to the EBV Western Blot "recomBlot EBV" developed by Mikrogen.

Other Western Blot procedures or staining methods can also be used.

Figure 3:
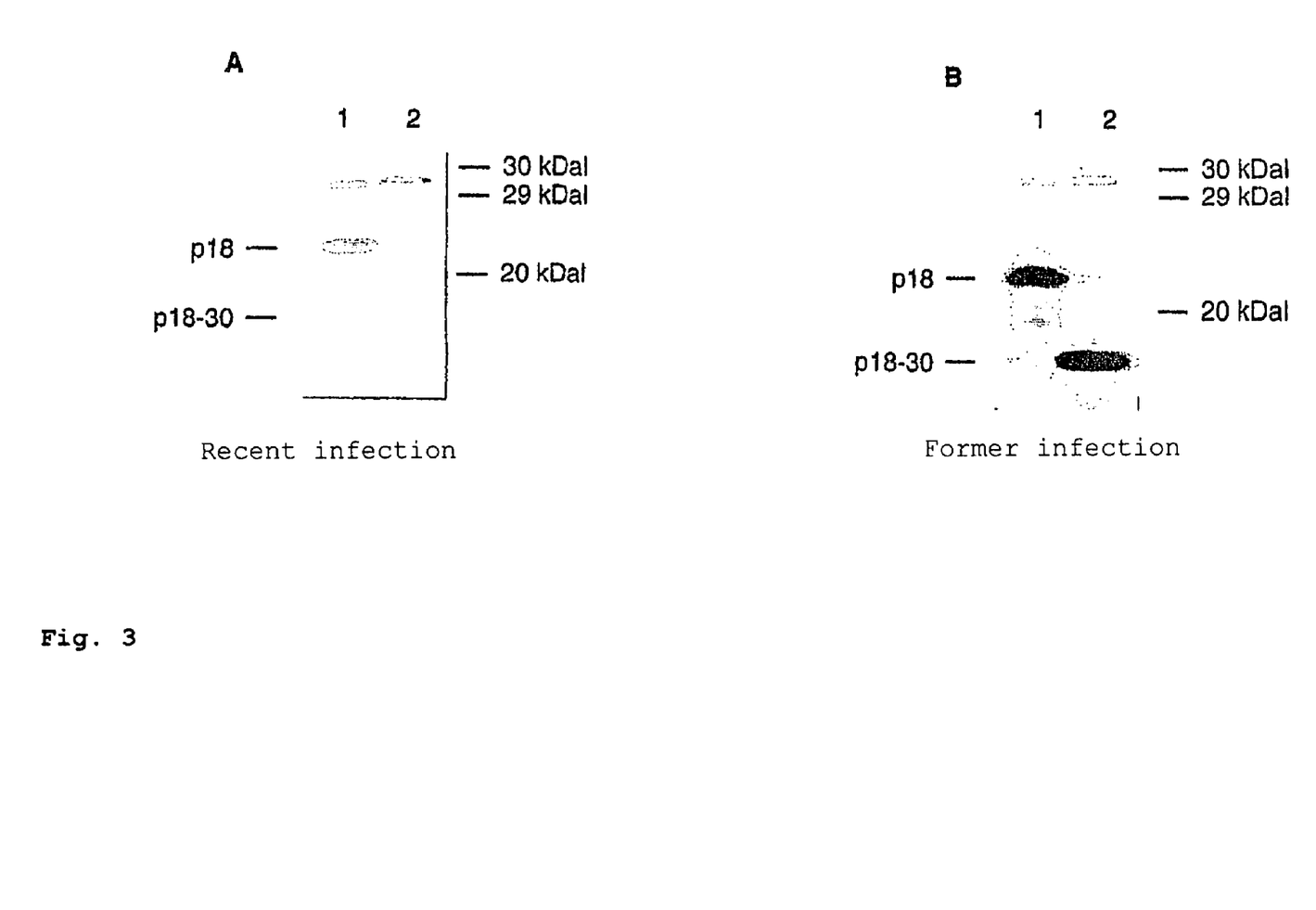

One serum each after recent infection (dating back about 3 weeks) and with infection dating back to the distant past (dating back about 1.5 years) was tested (FIG. 3).

Surprisingly, it is found here that the total p18 antigen has substantial differences in reactivity compared with the shortened version:

In the case of infection dating back to the distant past, both antigen variants react to about the same extent; in the case of sera of recent infections, however, only the total p18 antigen exhibits a substantial reaction.

There are therefore two markers (in addition to EBNA-1) which can be used for assigning the time of an EBV infection.

EXAMPLE 3

Comparison of a Reactivity using Commercially Available Immunodot Tests

The shortened variant of the p18 antigen was expressed in relatively large amounts and purified by means of conventional methods; the steps here were substantially the following:

lysis of the induced E. coli cells with the expression product;

separation of p18 as insoluble "inclusion bodies" by centrifuging;

washing of the insoluble pellet with various nonionic detergents;

dissolution of the remaining pellet with p18 in 8 M urea buffer;

various ion exchange chromatographies: DEAE, Q-sepharose, S-sepharose (all from Pharmacia).

The protein can thus be obtained in a purity of >99%.

Alternatively, other purification methods or sequences of column steps can also be used. With the use of the pQE30-p18 product, it is possible in particular to utilize the selective binding to Ni chelate columns.

The purified product was investigated in a line assay with regard to its reactivity with antibodies from persons with an EBV infection. For this purpose, the product was applied together with other recombinant EBV antigens (EBNA-1), p23-VCA, p138-EA, p54-EA) to nitrocellulose membranes by means of a so-called contact needle (Isoflow, from Imagene Inc.) in narrow lines and then further processed to give test strips (saturation of unbound areas on the membrane, application of markers, cutting into narrow strips). The test principle of the line assay corresponds to the commercially available immunoassay "recomLine EBV IgG" from Mikrogen (Article No. 4572).

The strips were tested with sera of recent EBV infections and past infections. For this purpose, the strips were incubated with serum diluted 1:1 00. After washing three times, incubation with anti-human-IgG (horseradish peroxidase conjugate) was carried out. After washing again (three times), incubation was effected with TMB substrate solution. As soon as the cut-off control band was visible, the substrate solution was removed and the strips were washed with water. A reaction is considered to be positive if the intensity of a band is equal to or greater than that of the cut-off control band. Thus, a peptide reacts with an antibody if a band intensity equal to the cut-off value or above the cut-off value is obtained. No reaction or a weak reaction means no band or a band with an intensity which is below the cut-off value. In this test, a cut-off value is defined in that the weak stain intensity of a so-called control band on the strip (cut-off band) is used as a limit for assessing the reactivity of the antigen bands (cf. for example the above-mentioned immunoassay "recomline EBV IgG" of Mikrogen). The faint staining of the cut-off band is always the same due to the use of certain reagents in the case of all procedures and patient samples.

A commercial strip test of Viramed, Planegg (EBV-ViraStripe), which is very similar to the strips described above but has in some cases other EBV antigens, including a total p18, was carried out for comparison.

Figure 4:
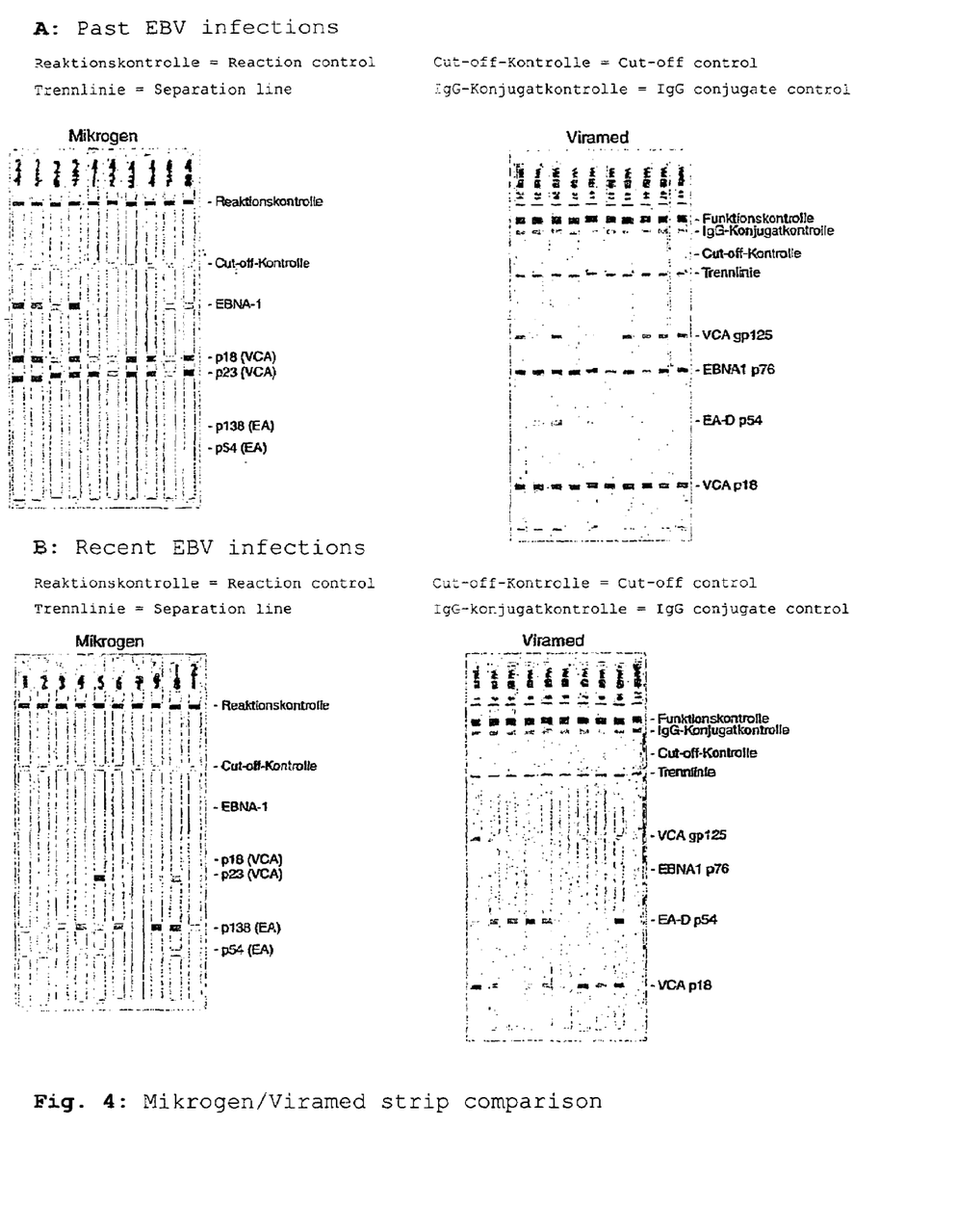
FIG. 4 shows a comparison of the reactivity of p 18 shortened at the N-terminus with a full-length p 18-VCA in a commercially available EBV antibody test based on strips (from Viramed, Planegg—ViraStripe EBV).

As is clearly evident from FIG. 4 with the immunostained strips, the total p18 (right) or the p18 shortened at the N-terminus (left) is equally well recognized in both tests of sera with past EBV infection, and the reactivities are very similar. On the other hand, the difference is substantial in the case of sera of persons having a recent EBV infection:

In the comparison test with conventional p18, this is recognized to a greater or lesser extent in all cases; on the strips with the shortened p18 antigen, a reaction is not to be found in any of the recent cases.

This once again underlines the value and reliability of the modified p18 for interpretation of the EBV status.

EXAMPLE 4

Figure 5:
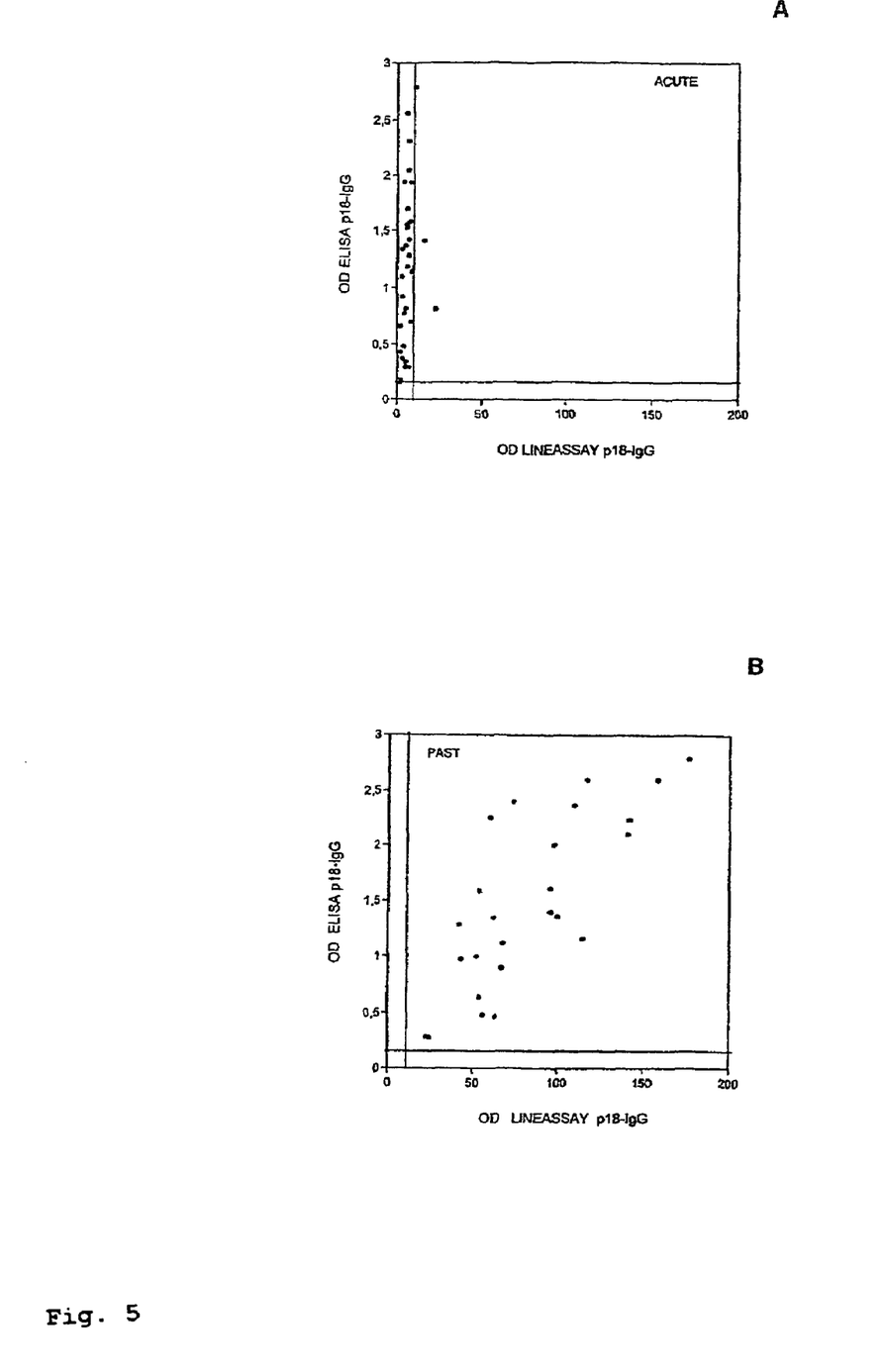
FIG. 5 shows a comparison of the reactivity of a test according to the invention with a commercially available ELISA system.

Comparison of Reactivity using a Commercially Available ELISA System 32 samples of patients with recent EBV infection ("acute") and 25 serum samples of persons with past (old) EBV infection were tested in each case with shortened p18 from Example 3 (sprayed on nitrocellulose strips, line assay p18) and a commercial ELISA (Epstein-Barr capsid antigen ETI-VCA-G; from DiaSorin) with conventional VCA antigen (FIG. 5).

In the two diagrams, in each case the ODs of both tests are plotted against one another. The x axis corresponds to the intensity of the band with the shortened p18. The y axis corresponds to the ELISA values with total p18.

The OD values of the ELISA were determined by means of a conventional ELISA reader and are between 0 and 3.0; the nitrocellulose strips with the shortened p18 were scanned in and the intensity of the band was determined by means of a software program; here, the scale comprises values from 0 to 200.

The two additional lines represent the respective cut-offs.

The differences in reactivity are clearly evident: In the case of the former infections, the reactivity distribution is similar to a high degree—highly positive sera in one test are generally also recognized by the other as being strongly positive—i.e. in the case of former infections, the ELISA antigen and the shortened p18 react in a very similar manner.

The picture in the case of the recent infections is dramatically different: in the case of the ELISA values—as well as in the case of the former infections—all values occur between cut-off and highly positive (OD 3.0); there is no difference compared with the picture in the case of past infections.

The OD values of the shortened p18 are, however, for the most part under the cut-off and only in two cases in the slightly positive region. This very impressively demonstrates the different reactivity of the shortened p18 in the case of recent and past infections.

EXAMPLE 5

Comparative Investigation of the p18 Reactivity in Different Test Formats

Figure 6:
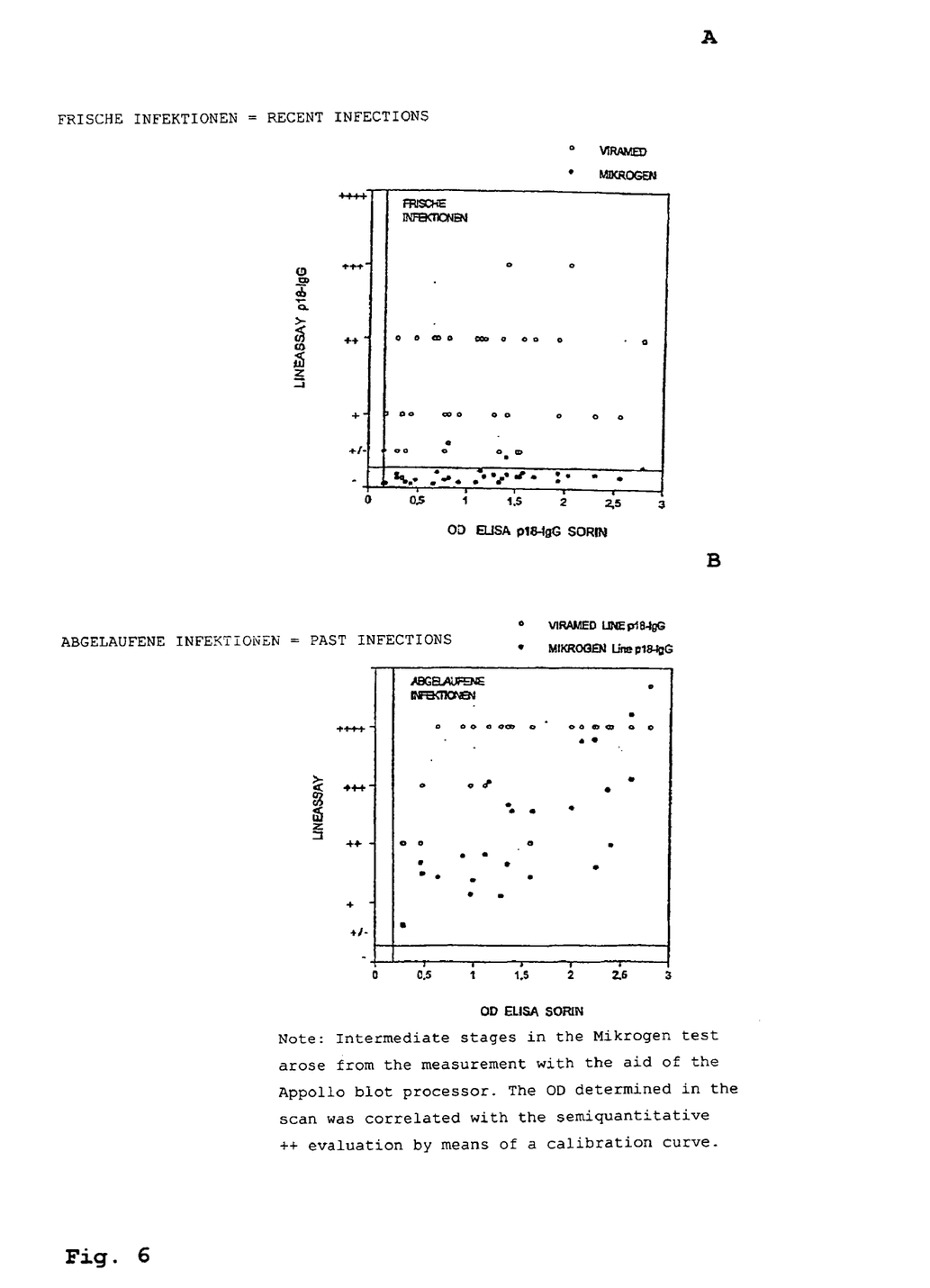

In a further study, the sera of recent and past infections from Example 4 were additionally investigated in strip tests using conventional VCA-p18 (from Viramed) and the results were correlated with the VCA-ELISA values and with the reactivity with the shortened p18 from Example 3 (FIG. 6).

The graphical evaluation was effected in a manner similar to that described in the preceding example:

The ELISA OD values are plotted along the x axis (from 0 to 3.0); the y axis corresponds to the p18 reactivities of the two strip tests (circles, total p18 (from Viramed), dots—shortened p18 antigen).

In the case of the picture of the sera with past infections, all sera are—as expected—ELISA-positive and at the same time also reactive in both test strips; i.e. the test format has no influence.

In the case of the sera of recent infections, however, the completely different reactivity of the shortened p18 is once again found: the ELISA values are scattered—as expected—in the region of the cut-off up to strongly reactive; the same pattern is shown by the sera in the test strip with total p 18; the shortened p18 antigen, on the other hand, is in the negative or—in the case of two samples—in the slightly positive region.

This evaluation once again very clearly demonstrates the inability of EBV test systems available to date to differentiate between past and recent infections with a VCA marker. By means of the measures described, a modified p18 antigen (shortened at the N-terminus) can make this differentiation.

Consequently, with the use of the shortened p18, a further, reliable marker for the diagnosis of a recent infection has been found in most cases, which marker, in combination with the known EBV markers, can produce a substantial improvement and reliability in the interpretation of the serological EBV status.

FURTHER LITERATURE REFERENCES

G. Bauer. Die Aussagemöglichkeiten der Epstein-Barr-Virus-Diagnostik [Potential information from Epstein-Barr virus diagnosis]Der Internist 33: 556-592 (1992)

G. Bauer. Epstein-Barr-Virus: Bedeutung und Möglichkeiten der Labordiagnostik [Importance and possibilities for laboratory diagnosis] Therapeutische Umschau 51: 558-562 (1994)

G. Bauer. Diagnostik der Herpesviren. Teil 1: Epstein-Barr-Virus (EBV) und Zytomegalievirus (CMV) [Diagnosis of herpes viruses. Part 1: Epstein-Barr virus (EBV) and cytomegalovirus (CMV)]. mta 10, 502-508 (1995).

G. Bauer. Diagnostik der Herpesviren. Teil II: Herpes simplex-Virus (HSV), Varizella-Zoster-Virus (VZV) und Humanes Herpesvirus-6 (HHV-6) [Diagnosis of herpes viruses. Part II: Herpes simplex virus (HSV), varicella zoster virus (VZV) and human herpes virus 6 (HHV-6)]. mta 10, 587-593 (1995)

G. Bauer. Rationale und rationelle EBV-Diagnostik [Rational and efficient EBV diagnosis]. Clin. Lab. 41, 623-634 (1995).

G. Bauer. IgM—ein variabler und mehrdeutiger diagnostischer Marker [IgM—a variable and ambiguous diagnostic marker]. Der Mikrobiologe 6: 44-51 (1996)

T. Walter, C. Gassmann, V. Vetter and G. Bauer. Avidity determination: utilization of a basic immunological mechanism allows to improve serological diagnosis of infections. Clin. Laboratory 43: 125-135, 1997.

M. Kampmann, K. Henninger and G. Bauer. Determination of antibodies directed specifically against Epstein-Barr virus nuclear antigen-1 (EBNA- 1) by anticomplementary immunofluorescence (ACIF). Med. Microbiol. Letters 2: 1-8 (1993)

M. Schillinger, M. Kampmann, K. Henninger, G. Murray, I. Hanselmann and G. Bauer. Variability of humoral immune response to acute Epstein-Barr virus (EBV) infection: evaluation of the significance of serological markers. Med. Microbiol. Letters 2: 296-303 (1993)

H.-J. Sohn and G. Bauer. Absorption of IgG increases the sensitivity of detection of the Epstein-Barr virus capsid antigen-specific IgM test. Med. Microbiol. Letters 2: 371-378 (1993)

V. Vetter, L. Kreutzer and G. Bauer. Differentiation of primary from secondary anti-EBNA-1-negative cases by determination of avidity of VCA-IgG. Clinical and Diagnostic Virology, 2: 29-39 (1994)

A. Anderson, V. Vetter, L. Kreutzer and G. Bauer. The avidities of IgG directed against viral capsid antigen (VCA) or early antigen (EA): useful markers for a more significant Epstein-Barr virus serology. J. Med. Virol. 43: 238-244 (1994)

G. Sigel, M. Schillinger, K. Henninger and G. Bauer. IgA directed against early antigen of Epstein-Barr virus is no specific marker for the diagnosis of nasopharyngeal carcinoma. J. Med. Virol. 43: 222-227 (1994)

W. Kamer and G. Bauer. Activation of a varicella zoster virus-specific IgA response during acute Epstein-Barr virus infection. J. Med. Virol. 44: 258-262 (1994).

C. Rapp, H. Berthold and G. Bauer. Loss of Anti-EBNA-1 during active hepatitis B virus infection. A diagnostic problem and indication for HBV-induced transient cellular immunosuppression. Med. Microbiol. Letters, 3: 235-243 (1994).

C. Alpers, C. Scheid and G. Bauer. Acute EBV infection results in IgM responses against unrelated viruses. Med. Microbiol. Letters 3: 306-314 (1994).

What is claimed is:

1. A new method for distinguishing between acute or recent EBV infection and old infection with EBV, comprising:
   reacting IgG antibodies of an individual with
   (a) the viral p18 antigen of the Epstein-Barr virus, and
   (b) a peptide which is derived from the viral p18 antigen of the Epstein-Barr virus, wherein said peptide is shortened at the N-terminus by 10 to 70 amino acids compared with the viral p18 antigen, or a fusion comprising the peptide and one or more further amino acids which do not correspond to the amino acid sequence of the viral p18 antigen, or a combination thereof;
   wherein strong binding to both (a) and (b) indicates old infection, and strong binding to (a) but not (b) indicates acute or recent EBV infection.

2. The method of claim 1, wherein the peptide of (b) comprises the amino acid sequence of SEQ ID NO:2.

\* \* \* \* \*

SEQUENCE LISTING

```
<160> NUMBER OF SEQ ID NOS: 6

<210> SEQ ID NO 1
<211> LENGTH: 176
<212> TYPE: PRT
<213> ORGANISM: Human herpesvirus 4

<400> SEQUENCE: 1

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
                20                  25                  30

Asn Asn Leu Pro Asn Asp Val Phe Arg Glu Ala Gln Arg Ser Tyr Leu
            35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ala Ser Ala Gly Thr Gly Ala
                100                 105                 110

Leu Ala Ser Ser Ala Pro Ser Thr Ala Val Ala Gln Ser Ala Thr Pro
            115                 120                 125

Ser Val Ser Ser Ser Ile Ser Ser Leu Arg Ala Ala Thr Ser Gly Ala
    130                 135                 140

Thr Ala Ala Ala Ser Ala Ala Ala Ala Val Asp Thr Gly Ser Gly Gly
145                 150                 155                 160

Gly Gly Gln Pro His Asp Thr Ala Pro Arg Gly Ala Arg Lys Lys Gln
                165                 170                 175

<210> SEQ ID NO 2
<211> LENGTH: 146
<212> TYPE: PRT
```

-continued

```
<213> ORGANISM: Artificial sequence
<220> FEATURE:
<223> OTHER INFORMATION: Primer

<400> SEQUENCE: 2

Asn Gln Asn Asn Leu Pro Asn Asp Val Phe Arg Glu Ala Gln Arg Ser
1               5                   10                  15

Tyr Leu Val Phe Leu Thr Ser Gln Phe Cys Tyr Glu Glu Tyr Val Gln
            20                  25                  30

Arg Thr Phe Gly Val Pro Arg Arg Gln Arg Ala Ile Asp Lys Arg Gln
        35                  40                  45

Arg Ala Ser Val Ala Gly Ala Gly His Ala His Leu Gly Gly Ser
    50                  55                  60

Ser Ala Thr Pro Val Gln Gln Ala Gln Ala Ala Ser Ala Gly Thr
65                  70                  75                  80

Gly Ala Leu Ala Ser Ser Ala Pro Ser Thr Ala Val Ala Gln Ser Ala
                85                  90                  95

Thr Pro Ser Val Ser Ser Ile Ser Ser Leu Arg Ala Ala Thr Ser
            100                 105                 110

Gly Ala Thr Ala Ala Ala Ser Ala Ala Ala Val Asp Thr Gly Ser
        115                 120                 125

Gly Gly Gly Gly Gln Pro His Asp Thr Ala Pro Arg Gly Ala Arg Lys
    130                 135                 140

Lys Gln
145

<210> SEQ ID NO 3
<211> LENGTH: 39
<212> TYPE: DNA
<213> ORGANISM: Artificial sequence
<220> FEATURE:
<223> OTHER INFORMATION: Primer

<400> SEQUENCE: 3
gagggatcca tcatgaaacg ccggctgccc aagcccacc                              39

<210> SEQ ID NO 4
<211> LENGTH: 33
<212> TYPE: DNA
<213> ORGANISM: Artificial sequence
<220> FEATURE:
<223> OTHER INFORMATION: Primer

<400> SEQUENCE: 4
cgcctgcagt tactgtttct tacgtgcccc gcg                                    33

<210> SEQ ID NO 5
<211> LENGTH: 30
<212> TYPE: DNA
<213> ORGANISM: Artificial sequence
<220> FEATURE:
<223> OTHER INFORMATION: Primer

<400> SEQUENCE: 5
gagggatccc tgaaccagaa taatctcccc                                        30

<210> SEQ ID NO 6
<211> LENGTH: 33
<212> TYPE: DNA
<213> ORGANISM: Artificial sequence
<220> FEATURE:
<223> OTHER INFORMATION: Primer
```

```
<400> SEQUENCE: 6
cgcctgcagt tactgtttct tacgtgcccc gcg                                33
```